(12) United States Patent
Mikkilineni

(10) Patent No.: US 8,323,175 B2
(45) Date of Patent: Dec. 4, 2012

(54) METHOD AND APPARATUS FOR INDUCING SLEEP

(76) Inventor: Maheswar R. Mikkilineni, Washington, DC (US)

( * ) Notice: Subject to any disclaimer, the term of this patent is extended or adjusted under 35 U.S.C. 154(b) by 0 days.

(21) Appl. No.: 13/188,420

(22) Filed: Jul. 21, 2011

(65) Prior Publication Data

US 2011/0282131 A1  Nov. 17, 2011

Related U.S. Application Data

(63) Continuation of application No. 12/259,285, filed on Oct. 27, 2008, now abandoned, which is a continuation-in-part of application No. 11/999,349, filed on Dec. 5, 2007, now abandoned, which is a continuation-in-part of application No. 11/449,519, filed on Jun. 8, 2006, now abandoned.

(51) Int. Cl.
*A61M 21/00* (2006.01)

(52) U.S. Cl. ......................................................... 600/26
(58) Field of Classification Search .............. 600/26–28; 128/897, 898
See application file for complete search history.

(56) References Cited

U.S. PATENT DOCUMENTS 7,422,014 B1 * 9/2008 Smith ....................... 128/204.23
2008/0319277 A1 * 12/2008 Bradley ......................... 600/301

* cited by examiner

*Primary Examiner* — Samuel Gilbert
(74) *Attorney, Agent, or Firm* — Kenneth H. Ohriner; Perkins Coie LLP

(57) ABSTRACT

Method to induce sleep, using devices that are worn on the nose and around the diaphragm. The nose-band is made of a soft, flexible and elastic material, such as perforated rubber, and is configured to fit onto the nose of a user. The diaphragm-band is made of a soft, flexible and elastic material, and is configured to fit over the diaphragm of a user.

7 Claims, 4 Drawing Sheets

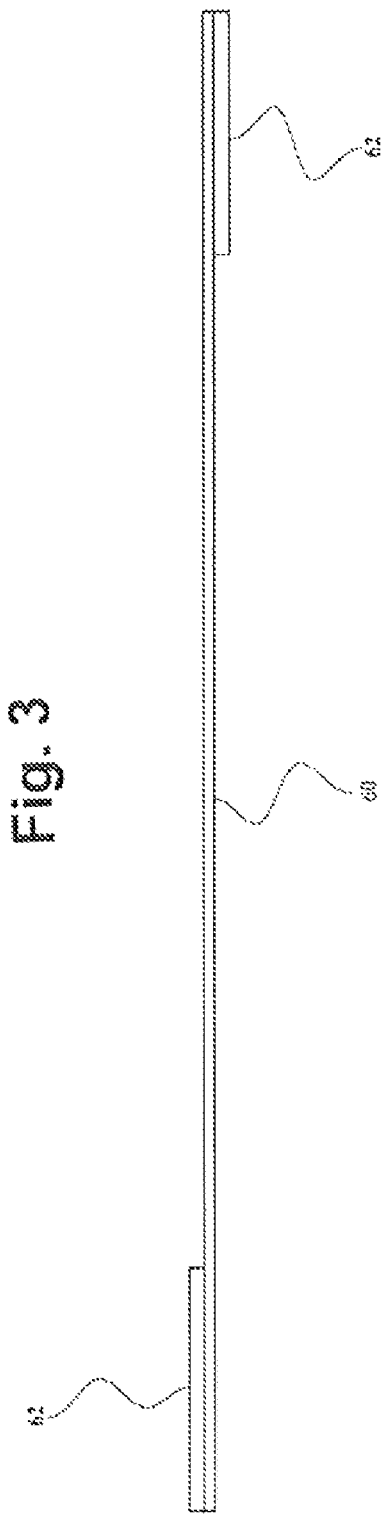

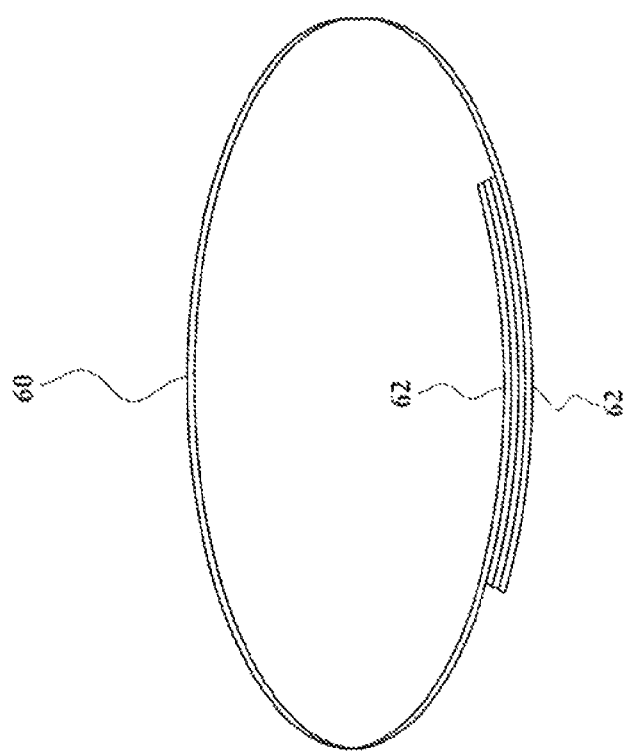

METHOD AND APPARATUS FOR INDUCING SLEEP

PRIORITY CLAIM

This application is a Continuation of U.S. patent application Ser. No. 12/259,285 filed Oct. 27, 2008 and, which is a Continuation-In-Part of application Ser. No. 11/999,349, filed Dec. 5, 2007, and now abandoned, which is a Continuation-In-Part of application Ser. No. 11/449,519, filed Jun. 8, 2006, and now abandoned. These Applications are incorporated herein by reference.

BACKGROUND OF THE INVENTION

The present invention relates to methods for inducing sleep, without the use of drugs.

Sleep-problems play a key-role in a large number of brain disorders. For example, strokes and asthma attacks tend to occur more frequently due to changes in hormones, heart rate, breathing rate, and other changes associated with sleep. Neurons that control sleep interact closely with the immune system—sleep may help body conserve energy that the immune system needs to mount an attack. Sleep problems occur in almost all people with mental disorders, including those with depression and schizophrenia. A person with depression is often awake in the night and unable to get back to sleep. Extreme sleep deprivation can lead to a seemingly psychotic state of paranoia and hallucinations in an otherwise healthy person, and disrupted sleep can trigger episodes of mania-agitation and hyperactivity, to a person with manic depression.

The National Sleep Foundation's (NSF) sleep in America poll found that 74% of American adults experience sleep problems a few nights a week or more, 39% get less than seven hours of sleep each weeknight, and more than one in three (37%) are so sleepy during the day that it interferes with daily activities. An article 'Counting sheep no aid to insomnia' published in January 2002, on the findings of Oxford study on sleep, reported that "1 in 10 suffer from chronic insomnia and it is estimated that sleeplessness costs the US economy $35 billions a year . . . ." The brain requires a sleep-cycle, deep sleep (DS) and rapid eye movement (REM) sleep, of about eight hours in a 24-hour day to function properly. A recent study at Harvard Medical School and University of California concludes" . . . a lack of sleep causes the brain's emotional centers to dramatically overreact . . . (with) psychiatric disorders . . . (and) fractures the brain mechanisms that regulate key aspects of mental health . . . and, sleep appears to restore emotional brain's circuits."

Currently, there are several prescription drugs available to aid sleep. They can shorten the time it takes to fall asleep and reduce awakenings, which adds to total time spent asleep. Possible side effects include feeling tired or drowsy the next day, memory loss, headache and problems with performance. Prescription sleeping pills can cause strange and potentially dangerous side effects. Those side effects can include dangerous allergic reactions and bizarre behaviors such as sleep eating, walking and driving, in which a person will drive a car while not fully awake and has no memory of doing so.

SUMMARY OF THE INVENTION

There are two devices in this invention—one to use on the nose, and the other to use on the diaphragm, during practicing the process, which makes the user go to sleep, this helping to alleviate mental disorders and strokes.

Use of the nose-device and the diaphragm-device makes one breath freely and deeply. This provides more oxygen into the lungs, and into the blood-stream to alleviate problems caused by peripheral neuropathy.

BRIEF DESCRIPTION OF THE DRAWINGS

FIG. 3 is a plan-view of the diaphragm-device.

FIG. 4 is a top-view of the diaphragm-device when put on the diaphragm.

DETAILED DESCRIPTION OF THE DRAWINGS

The user places a nose-band on his (or her) nose 10. The user also places a diaphragm-band on his (or her) diaphragm. The user lies down and closes the eyes. As a result, the user then goes to sleep 20.

In this method to induce sleep, a person is required to put on the devices, lay in bed (or sofa) and close eyes and keep them closed to cut off incoming light into the eyes and get dark-night's sleep.

Figure 1:
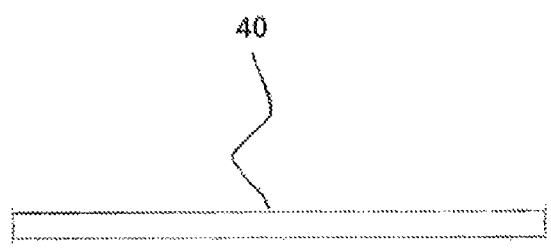
FIG. 1 is a front-view of the nose-device when put on the nose.
Figure 2:
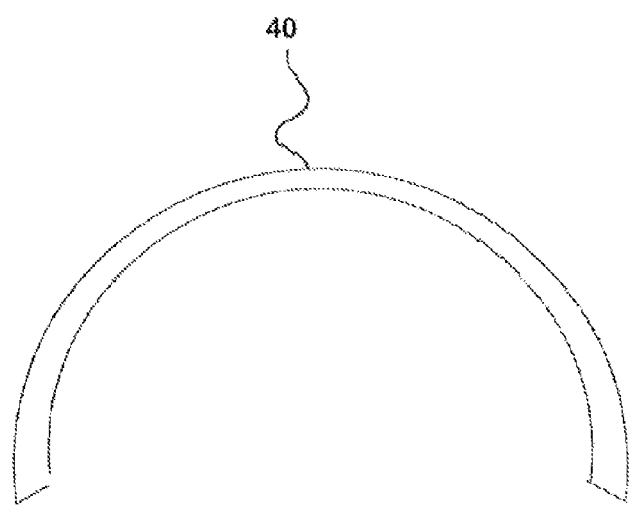
FIG. 2 is a plan-view of the nose-device before it is put on the nose.

Two devices are used in this method. The device to be worn on the nose is shown in FIGS. 1 and 2. It is made of a soft, flexible and elastic material. It is a band 40, configured to fit on to various nose-sizes, with self-adhesive to stay stuck on to skin and keep it comfortably on the nose while in use. The nose-band is made from rubber or equal, or any other suitable materials. The device elongates or contracts sufficiently to facilitate the user breathing air freely through the nose and deeply into the lungs. The nose-band is re-usable to help the user concentrate the mind on the device or inhalation-exhalation of the breath.

The other device used in this method, shown in FIGS. 3 and 4, is worn around the diaphragm. In FIG. 3 the diaphragm-band is shown in an open position, with the ends not joined. In FIG. 4 the diaphragm-band is shown in a closed position, with the ends joined, when it is worn around the diaphragm. It is made of a soft, flexible and elastic material. It is a band 60 configured to fit around various diaphragm-sizes, with self-adhesive ends 62, to stay stuck together and keep it comfortably on the diaphragm while in use.

The diaphragm-band is made from rubber or equal, or any other suitable material. The device elongates or contracts sufficiently to facilitate the user breathing air freely through the nose and deeply into the lungs. The diaphragm-band is re-usable to help the user concentrate the mind on the device or movement of the diaphragm while inhaling and exhaling.

In learning the method, a person can perform the following steps: The person lays in bed (or sofa) with closed-eyes, and visualizes upon a principal thought, such as on the nose-band or inhalation and exhalation of breath, until a calm mind is attained with decrease of intrusive thoughts in the mind. That practice should continue on the nose-band or inhalation and exhalation of breath or with different principal thoughts, one at a time, until one-thought which works consistently is identified. The person thinks positively in the mind and by visualizing one principal thought about any object-thing, location-spot, or action-item that exists within or without, for example the device on the nose or inhale-exhale of the breath. The person generates positive-signals in the mind by visualizing two or more principal thoughts calmly-equally at the same time, for example the device on the nose or inhalation-exhalation of the breath, and the device on the diaphragm or movement of diaphragm, until one-set of thoughts which works consistently is identified.

It is to be understood that the present invention is not limited to the sole embodiment described above, but encompasses any and all embodiments within the scope of the following claims.

What is claimed is:

1. A method of inducing sleep, comprising the steps of:
   (a) placing on the nose of a user a nose-band with adhesive end-cups that stick to the skin;
   (b) placing a band over the diaphragm of the user, the diaphragm-band having two ends that overlap and can be joined together by self-adhesive;
   (c) wherein the user is required to lay down and close the user's eyes at the start of step and keep them closed through to cut off incoming light into the eyes and
   (d) visualizing the nose-band during inhale and exhale of breath and at the same time visualizing the band over the diaphragm to induce sleep of the user.

2. The method of inducing sleep according to claim 1, wherein the nose-band is made of a soft, flexible and elastic material, and is configured to fit onto the nose of a user.

3. The method of inducing sleep according to claim 2, wherein the soft, flexible and elastic material is perforated rubber.

4. The method of inducing sleep according to claim 1, wherein the diaphragm-band is made of a soft, flexible and elastic material, and is configured to fit over the diaphragm of a user.

5. The method of inducing sleep according to claim 4, wherein the soft, flexible and elastic material is perforated rubber.

6. The method of inducing sleep according to claim 1, wherein the nose-band and the diaphragm-band are sufficiently elastic that the ends stay stuck and keep in position while in use for breathing air freely through the nose and deeply into the lungs.

7. A method of inducing sleep, comprising the steps of:
   (a) placing a nose band on the nose of a user;
   (b) placing a band around the torso of the user, the band having two ends that overlap and can be secured together;
   (c) wherein the user is lies down and closes the user's eyes and
   (d) visualizing the nose-band during inhale and exhale of breath and at the same time visualizing the band around the torso to induce sleep of the user.

* * * * *